US008938291B1

(12) United States Patent
Azarnasab et al.

(10) Patent No.: US 8,938,291 B1
(45) Date of Patent: Jan. 20, 2015

(54) METHODS AND SYSTEMS FOR SIGNAL PROCESSING OF NEURAL DATA

(75) Inventors: Ehsan Azarnasab, Salt Lake City, UT (US); Erik Alfonso Nilsen, McKinney, TX (US)

(73) Assignee: Blackrock Microsystems, LLC, Salt Lake City, UT (US)

( * ) Notice: Subject to any disclaimer, the term of this patent is extended or adjusted under 35 U.S.C. 154(b) by 789 days.

(21) Appl. No.: 12/906,673

(22) Filed: Oct. 18, 2010

Related U.S. Application Data

(60) Provisional application No. 61/252,578, filed on Oct. 16, 2009.

(51) Int. Cl.
*A61B 5/0476* (2006.01)
*H03K 5/00* (2006.01)
*G06F 9/455* (2006.01)
*A61B 5/00* (2006.01)
*A61B 5/04* (2006.01)
*A61B 5/048* (2006.01)

(52) U.S. Cl.
CPC ........... *A61B 5/7217* (2013.01); *A61B 5/04017* (2013.01); *A61B 5/0476* (2013.01); *A61B 5/048* (2013.01); *G06F 9/455* (2013.01)
USPC .............. 600/544; 327/551; 327/553; 703/20

(58) Field of Classification Search
CPC ........... A61B 5/04012; A61B 5/04014; A61B 5/04017; A61B 5/0476; A61B 5/048; A61B 5/0006; A61B 5/7203; A61B 5/7217; G06F 3/015; G06F 17/18; G06F 19/345
USPC .......................................................... 600/544
See application file for complete search history.

(56) References Cited

U.S. PATENT DOCUMENTS

| 6,016,080 | A  | * | 1/2000  | Zuta et al. ........................ 331/25  |
| 6,188,499 | B1 | * | 2/2001  | Majima .......................... 398/208 |
| 2007/0100278 | A1 | * | 5/2007  | Frei et al. ........................ 604/66 |
| 2008/0309376 | A1 | * | 12/2008 | Song et al. ....................... 327/2  |

* cited by examiner

*Primary Examiner* — Charles A Marmor, II
*Assistant Examiner* — Michael J Burrage
(74) *Attorney, Agent, or Firm* — Dorsey & Whitney LLP

(57) ABSTRACT

In an embodiment, an electrical-line-noise canceller includes a phase detector, a phase lock loop, a zero-crossing detector, and an adaptive filter. The phase detector is configured to receive a composite input signal including an input neural signal combined with electrical line noise and to detect a phase of the electrical line noise. The phase lock loop is coupled to the phase detector and is configured to lock to the phase of the electrical line noise. The zero-crossing detector is coupled to the phase lock loop and is configured to detect zero crossings of an output of the phase lock loop. The adaptive filter is coupled to the zero-crossing detector and is configured to remove the electrical line noise from the composite input signal and output a filtered neural signal that is substantially similar to the input neural signal.

8 Claims, 8 Drawing Sheets

METHODS AND SYSTEMS FOR SIGNAL PROCESSING OF NEURAL DATA

CROSS-REFERENCE TO RELATED APPLICATIONS

This application claims the benefit of U.S. Provisional Application No. 61/252,578 filed on 16 Oct. 2009, the disclosure of which is incorporated herein, in its entirety, by this reference.

BACKGROUND

Some neuralphysiological data acquisition systems are configured to record and analyze animal or human brain and/or peripheral-nerve electrical activity. Such systems typically include one or more sensors that generate neural signals indicative of the brain or peripheral-nerve electrical activity near the sensor. Neural signals generated by the sensors can be collected and processed to assist in the study of, for example, sensory perception, motor control, learning and memory, attention, cognition and decision making, drug and toxin effects, epilepsy, Parkinson's, neuroprosthetics, brain-machine interfaces, neurostimulation therapies, dystonia, traumatic brain injury, and stroke.

In some instances, a power supply of the neuralphysiological data acquisition system may add noise to the neural signals that can interfere with the processing and use of the neural signals. For example, when the neuralphysiological data acquisition system is plugged into a wall socket to access mains electricity, e.g., a general-purpose alternating current ("AC") electric power supply, the line frequency of the mains electricity can manifest itself as noise that combines with the neural signals. Noise resulting from the line frequency of the mains electricity or other power supply is an example of electrical line noise.

In the United States and various other countries, the mains electricity has a nominal line frequency of 60 Hz. In many other countries in the world, the mains electricity has a nominal line frequency of 50 Hz. In both cases, the actual line frequency of the mains electricity at any given time is typically somewhere within a range defined by the nominal line frequency plus or minus a frequency deviation. In the United States, for instance, the actual line frequency at any given time is typically within a range defined as 60 Hz±3 Hz.

Thus, the actual frequency of electrical line noise in neural signals collected by a neuralphysiological data acquisition system is not constant and can therefore be difficult to filter from the neural signals.

SUMMARY

Some embodiments generally relate to neural signals and include an electrical-line-noise canceller configured to filter electrical line noise from neural signals and to neuralphysiological data acquisition systems configured to acquire neural signals.

In an embodiment, an electrical-line-noise canceller includes a phase detector, a phase lock loop, a zero-crossing detector, and an adaptive filter. The phase detector is configured to receive a composite input signal including an input neural signal combined with electrical line noise and to detect a phase of the electrical line noise. The phase lock loop is coupled to the phase detector and is configured to lock to the phase of the electrical line noise. The zero-crossing detector is coupled to the phase lock loop and is configured to detect zero crossings of an output of the phase lock loop. The adaptive filter is coupled to the zero-crossing detector and is configured to remove the electrical line noise from the composite input signal and output a filtered neural signal that is substantially similar to the input neural signal.

In an embodiment, a neuralphysiological data acquisition system includes an electrode array, a digitizer/amplifier module, and a neural signal processor. The electrode array is configured to receive and transmit analog neural signals. The digitizer/amplifier module is coupled to the electrode array and is configured to amplify and convert the analog neural signals to digital neural signals. The neural signal processor includes an electrical-line-noise canceller coupled to the digitizer/amplifier module and configured to receive a composite input signal including the digital neural signals and electrical line noise. The electrical-line-noise canceller is further configured to selectively filter the electrical line noise from the composite input signal and output filtered neural signals.

In an embodiment, a method of filtering electrical line noise from a composite input signal includes receiving a composite input signal from a microelectrode array of a neuralphysiological data acquisition system. The composite input signal includes a neural signal and electrical line noise. The method further includes filtering the electrical line noise from the composite input signal without substantially modifying the neural signal.

In an embodiment, a method of manipulating stored neural signal data includes acquiring a neural signal from a neuralphysiological data acquisition system. The method further includes storing the neural signal on a computer-readable medium as stored neural signal data. The method further includes emulating signal processing firmware of the neuralphysiological data acquisition system with signal processing software executed by a computing device. The method further includes performing signal processing on the stored neural signal data using the signal processing software.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical elements or features in different views or embodiments shown in the drawings.

DETAILED DESCRIPTION

Embodiments of the invention relate to methods that selectively manipulate neural data acquired from a neuralphysiological data acquisition system. Systems that implement such methods, such as in neuralphysiological data acquisition systems employing microelectrode arrays, are also disclosed.

I. Line-Noise Cancellation

Figure 1:
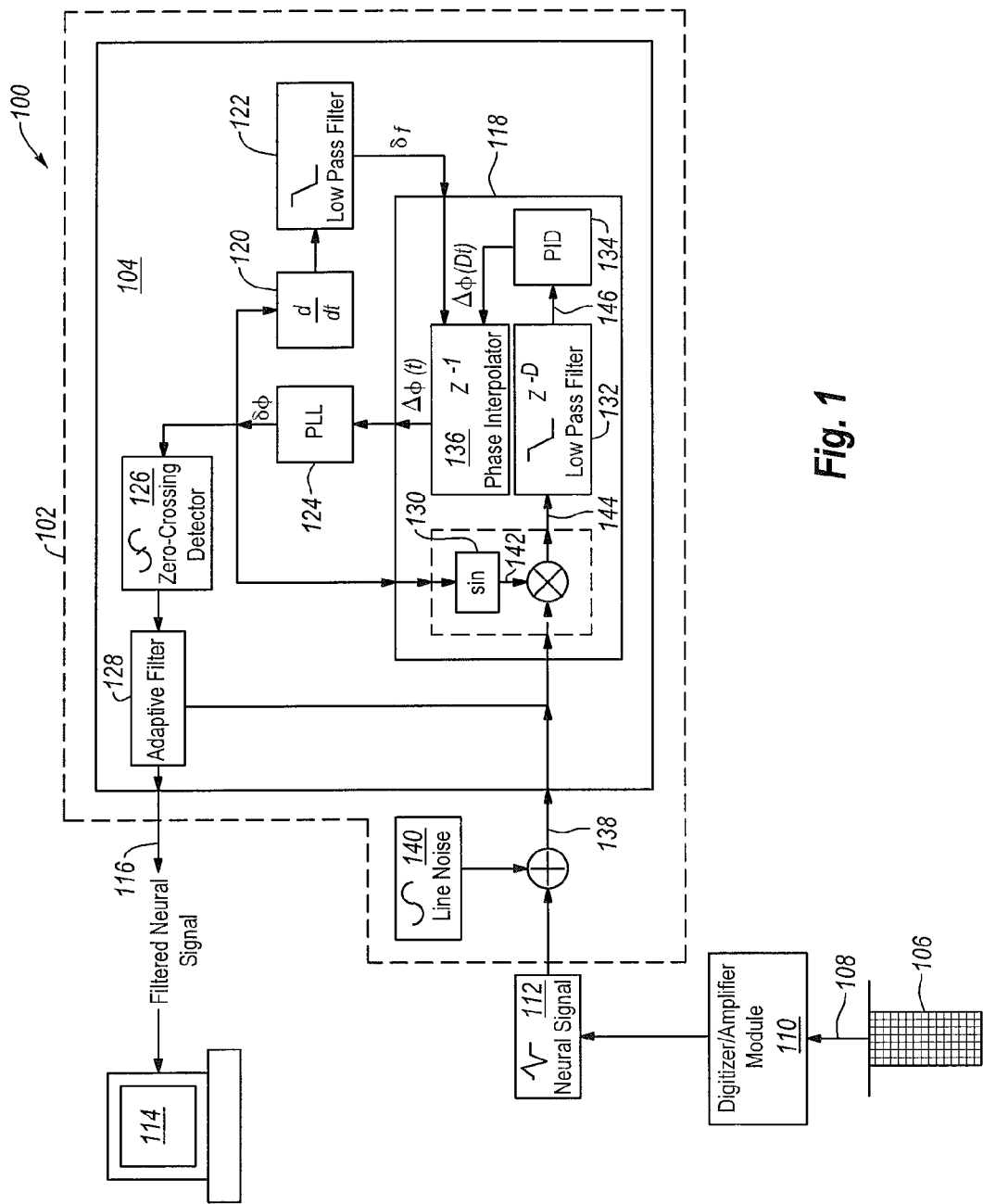
FIG. 1 is a functional block diagram of an embodiment of a neuralphysiological data acquisition system that includes an electrical-line-noise canceller configured to execute an electrical-line-noise cancellation algorithm.

FIG. 1 is a functional block diagram of a first embodiment of a neuralphysiological data acquisition system 100 (hereinafter "system 100"). The system 100 includes a neural signal processor 102 that includes an electrical-line-noise canceller 104 configured to execute an electrical-line-noise cancellation algorithm that selectively filters non-biological electrical signals from a composite signal. For example, the electrical-line-noise cancellation algorithm may be executed by firmware of the neural signal processor 102, or by software including computer-executable instructions stored on a computer-readable medium for executing the algorithm by a processor of, for example, a desktop or laptop computer.

The system 100 further includes an array of microelectrodes 106 (hereinafter "array 106") configured to receive and transmit one or more analog neural signals 106, and a digitizer/amplifier module 108 coupled to the array 106 and configured to amplify and convert the analog neural signals 108 to one or more digital neural signals 112. For example, the array 104 may be suitably configured to acquire analog neural signals 108 from brain tissue or peripheral nerve tissue. The system 100 further includes a general purpose or special purpose computer 114 (e.g., a desktop or laptop computer) coupled to receive one or more filtered neural signals 116 processed by the neural signal processor 102 and configured to display the filtered neural signals 116 for a user, such as a medical professional or researcher.

One example of a suitable neuralphysiological data acquisition system that may include a neural signal processor including firmware configured to execute embodiments of the disclosed electrical-line-noise cancellation algorithm is marketed by Blackrock Microsystems as the Cerebus™ Data Acquisition System. Details about the Cerebus™ Data Acquisition System are described in the Cerebus™ Data Acquisition System Users Manual, Revision 9.00, which users manual was submitted as an appendix to the 61/252,578 provisional application on Oct. 16, 2009 and is incorporated herein, in its entirety, by this reference.

In the illustrated embodiment of FIG. 1, the electrical-line-noise canceller 104 includes a phase detector 118, a differentiator 120, a first low pass filter 122, a phase lock loop ("PLL") 124, a zero-crossing detector 126, and an adaptive filter 128. As further shown in FIG. 1, the phase detector 118 includes a sinusoid generator 130, a second low pass filter 132, a proportional-integral-derivative ("PID") controller 134, and a phase interpolator 136.

In operation, a composite input signal 138 processed by the electrical-line-noise canceller 104 is modeled in some embodiments as a superposition of a digital neural signal 112 and an electrical-line-noise waveform 140. The main frequency of the electrical-line-noise waveform 140 in these and other embodiments is a sinusoid having a nominal frequency of, e.g., 50 or 60 Hertz ("Hz") (plus a frequency drift), and an unknown phase. Therefore, the composite input signal 138 x(t) can be modeled as:

$$x(t)=N(t)+A(t)\sin(2\pi(f_{LN}+\delta f(t))t+\delta\phi(t)), \quad \text{Eq. 1}$$

where N(t) is the digital neural signal 112, A(t) is the amplitude signal of electrical-line-noise waveform 120, and $f_{LN}$ is the nominal line noise frequency. In addition, $\delta f(t)$ is the frequency deviation from nominal frequency $f_{LN}$, also referred to as residual frequency, and $\delta\phi(t)$ is phase deviation, also referred to as residual phase.

The composite input signal 138 is processed by phase detector 118 in some embodiments as follows. A sinusoid 142 is generated by the sinusoid generator 130 with a nominal frequency. According to some examples, the sinusoid 142 is modeled by the equation:

$$y(t)=\cos(\phi(t)-\pi/2), \quad \text{Eq. 2}$$

where $\phi(t)$ is estimated phase and is an estimation of the main electrical line noise harmonics and may be calculated for each incoming sample.

In some embodiments, the estimated phase $\phi(t)$ is modeled by:

$$\phi(t)=2\pi*f_{LN}*t+\Delta\phi(t), \quad \text{Eq. 3}$$

where $\Delta\phi(t)$ is phase difference and may refer to estimated phase difference $\Delta\phi_e(t)$ output by the PID controller 136 once every D samples, or interpolated phase difference $\Delta\phi_i(t)$ output by the phase interpolator 136 for every sample in between the D-sampled estimated phase difference $\Delta\phi_e(t)$. Alternately or additionally, phase difference $\Delta\phi(t)$ may refer to phase deviation $\delta\phi(t)$ in embodiments that include a PLL 124. Example formulas for modeling the estimated phase difference $\Delta\phi_e(t)$ and interpolated phase difference $\Delta\phi_i(t)$ according to some embodiments are provided below.

The composite input signal 138 is multiplied to the sinusoid 142, called "demodulation," to produce a demodulated noise signal 144. In some embodiments, the demodulated noise signal 144 is a baseband signal, meaning the frequency of the demodulated noise signal 144 is near zero Hz. The demodulated noise signal 144 is filtered by second low pass filter 132, resulting in an error signal 146 with a residual phase difference. Because of filter group delay of the second low pass filter 132, the output of the second low pass filter 132 may only be considered to be valid about every D samples. In some examples, D is 1800 samples. Alternately or additionally, D is a different number depending on the parameters of electrical-line-noise canceller 104.

The error signal 146 may be modeled in some examples by the equation:

$$\text{error}(t)=B(t)\sin(\Delta\phi_e(t)), \quad \text{Eq. 4}$$

where B(t) is an approximation of A(t) in equation 1 above. Alternately or additionally, B(t) is substantially equal to A(t). The estimated phase difference $\Delta\phi_e(t)$ represents the absolute error that may be minimized by the electrical-line-noise canceller 104 according to some embodiments. Alternately or additionally, when B(t) is greater than zero and Δφ(t) is near zero, the equation for error(t) approximates the actual error.

In some embodiments, a function of the inner loops of electrical-line-noise canceller 104 is to minimize the phase difference between the sinusoid 142 and the electrical-line-noise waveform 140 so as to lock to the phase of the electrical-line-noise waveform 140. In particular, a function of the inner loops of electrical-line-noise canceller 104 may be to drive the phase difference Δφ(t) to zero.

The PID controller 134 applies a slow PID algorithm to determine the estimated phase difference $\Delta\phi_e(t)$ at the output of the second low pass filter 132. In particular, in some examples the PID controller 134 estimates the phase difference $\Delta\phi_e(t)$ every D samples. The estimated phase difference $\Delta\phi_e(t)$ output by PID controller 134 may be modeled in some embodiments by the equation:

$$\Delta\phi_e(t)=K_p*\text{error}(t=n*D)+K$$
$$i*(\Delta\phi_e(t=n*D-D)+\text{error}(t=n*D)*1/f_s)+K_d*(\text{error}(t=n*D)-\text{error}(t=n*D-D)),\qquad \text{Eq. 5}$$

where $K_p$, $K_i$, and $K_d$ are the proportional, integral and derivative weighting factors of the PID controller 134, n is 0, 1, 2, 3, ..., error(t=n*D) is the output of the second low pass filter 132 at a particular valid time sample t=n*D, $\Delta\phi_e(t=n*D-D)$ is the estimated phase difference $\Delta\phi_e(t)$ at an immediately preceding valid time sample t=n*D−D, $f_s$ is the sampling frequency, and error(t=n*D−D) is the output of the second low pass filter 132 at the immediately preceding valid time sample t=n*D−D.

In some embodiments, the estimated phase difference $\Delta\phi_e(t)$ is unwrapped and calculated once for every D samples and provided as input to the phase interpolator 136. Accordingly, the PID controller 134 provides the estimated phase difference $\Delta\phi_e(t)$ to the phase interpolator 136 once every D samples according to some embodiments.

The phase interpolator 136 receives the estimated phase difference $\Delta\phi_e(t)$ once every D samples from the PID controller 134 and in response to receiving the estimated phase difference $\Delta\phi_e(t)$ once every D samples, outputs the estimated phase difference $\Delta\phi_e(t)$ to the PLL 124.

The phase interpolator 136 additionally receives estimated frequency deviation δf(t) for every sample from the first low pass filter 122. The estimated frequency deviation δf(t) received from the low pass filter 122 is used by the phase interpolator 136 to linearly interpolate and find the interpolated phase difference $\Delta\phi_i(t)$ for every sample in between the estimated phase differences $\Delta\phi_e(t)$ received from the PID controller 134.

In some examples, the interpolated phase difference $\Delta\phi_i(t)$ is modeled by the equation:

$$\Delta\phi_i(t)=\Delta\phi_e(t=n*D)+2\pi*(f_{LN}+\delta f(t))*(n*D-D),\qquad \text{Eq. 6}$$

where all of the constants and variables of equation 6 are as already set forth above.

The PLL 124 receives the phase difference Δφ(t) (e.g., either $\Delta\phi_e(t)$ or $\Delta\phi_i(t)$) output by the phase interpolator 136 and fine tunes the phase difference to lock to the phase of the electrical-line-noise waveform 140. The PLL 124 outputs phase deviation δφ(t), which in some embodiments is a more accurate version of the phase difference Δφ(t) received from the phase interpolator 136. The phase deviation δφ(t) output by PLL 124 is provided to the sinusoid generator 130, the zero-crossing detector 126, and the differentiator 120.

The sinusoid generator 130 changes the estimated phase φ(t) of the sinusoid 142 consistent with the phase deviation δφ(t) received from the PLL 124.

The differentiator 120 differentiates two consecutive sampled outputs of the phase deviation δφ(t) and outputs unfiltered frequency deviation δf(t) to the low pass filter 122.

The low pass filter 122 filters the unfiltered frequency deviation δf(t) to remove noise from the calculation of frequency deviation δf(t) and outputs frequency deviation δf(t). The frequency deviation δf(t) is fed back to the phase interpolator 136. Although not mentioned previously, in some embodiments the interpolated phase difference $\Delta\phi_i(t)$ output by phase interpolator 136 is delayed by one sample.

The zero-crossing detector 126 receives the phase deviation δφ(t) from PLL 124 and detects the zero crossings of the phase deviation δφ(t). In some examples, the zero-crossing detector 126 detects a zero crossing when the phase deviation δφ(t) is below a predetermined threshold and/or a predetermined minimum number of samples have occurred since the last detected zero crossing. The predetermined threshold may be $2\pi*f_{LN}/f_s$ and/or the predetermined minimum number of samples may be 256 samples. Of course, the specific values for the predetermined threshold and predetermined minimum number of samples are provided by way of example only and should not be construed to limit the invention.

When a zero crossing is marked, lock occurs and the adaptive filter 128 removes the electrical-line-noise waveform 140 from the composite input signal 138 and outputs filtered neural signals 116. In some embodiments, the adaptive filter 128 estimates the electrical-line-noise waveform 140 by a running average over the composite input signal 138 for one cycle (e.g., one period of the electrical-line-noise waveform 140) beginning at each detected zero crossing and then removing the average from the composite input signal 138.

In some instances, the zero-crossing detector 126 is unable to detect and mark a zero crossing. According to some embodiments, the adaptive filter 128 is configured to stop filtering until the next zero crossing is marked. In these and other embodiments, artifacts may be introduced in the filtered neural signals 116.

Alternately, and to at least partially reduce artifacts in the filtered neural signals 116 output by the adaptive filter 128, the adaptive filter 128 is configured to re-use the previous running average to filter the composite input signal 138 until the next zero crossing is marked. In particular, when a zero crossing is not marked, the adaptive filter 128 is unable to calculate a running average for a cycle of the composite input signal 138. Instead, the adaptive filter 128 subtracts the previously calculated running average from the composite input signal 138 until the next zero crossing is marked and the adaptive filter 128 resumes normal operation.

Example Embodiment

The following example embodiment provides further detail in connection with a specific embodiment of the neural signal processor 102. The further details regarding the following example embodiment are provided by way of illustration only, and not by way of limitation.

According to one example embodiment, the second low pass filter 132 is an infinite impulse response ("IIR") filter. In the example embodiment, the second low pass filter 132 has filter coefficients B1, B2, A1, and A2 that are respectively equal to about 1.0, 0.0, −0.999441650429352 and 0.0. Additionally, the second low pass filter 132 has a gain that is equal to about 0.000279174785324 and a group delay D of 1800 for passband frequencies.

According to the example embodiment, the PID controller 134 has a proportional weighting factor $K_p$ of 24.0, an integral weighting factor $K_i$ of 1.0, and a derivative weighting factor $K_d$ of 0.2.

In the example embodiment, the PLL 124 is a second-order PLL and has a noise bandwidth BL of 2.4, a damping factor ZETA of 0.9, a coefficient BETA of −1.0, and a coefficient MU of $1/f_s$. From the foregoing, natural frequency OMEGA, gain KL and coefficient ALPHA of the PLL 124 can be determined as follows:

$$OMEGA = (2*BL/(ZETA+1/(4*ZETA))), \quad \text{Eq. 7}$$

$$KL = (OMEGA^2/f_s + 2*ZETA*OMEGA), \quad \text{Eq. 8}$$

$$ALPHA = (-2*ZETA/(2*ZETA+OMEGA/f_s)). \quad \text{Eq. 9}$$

Experimental Results

FIGS. 2-5 include various graphs corresponding to various outputs of the neural signal processor 102 of FIG. 1 produced in response to processing a particular digital neural signal 112 using the specific example embodiment of the neural signal processor 102 set forth above.

Figure 2:
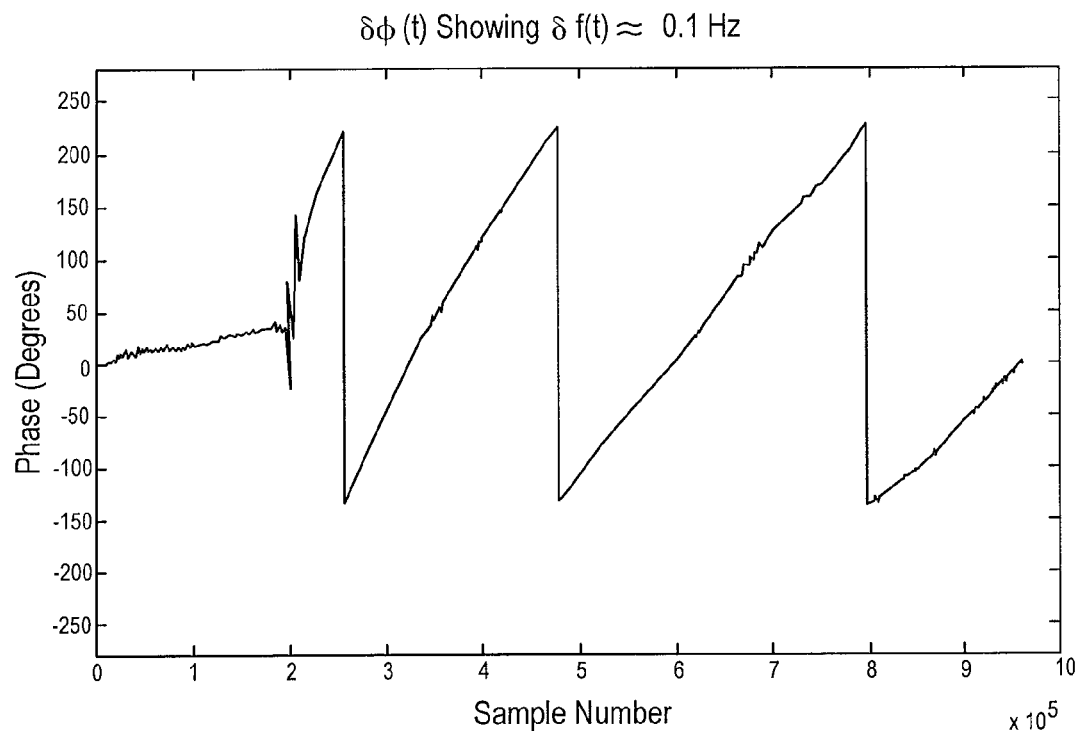
FIG. 2 is a graph of a wrapped phase deviation $\delta\phi(t)$ output by a phase lock loop of the electrical-line-noise canceller of FIG. 1 including data which shows significant line noise.

In particular, FIG. 2 shows the wrapped phase deviation 60) output by the PLL 124. FIG. 2 includes data which shows significant line noise and from which a frequency deviation δf(t) of about 0.1 Hz can be derived.

Figure 3:
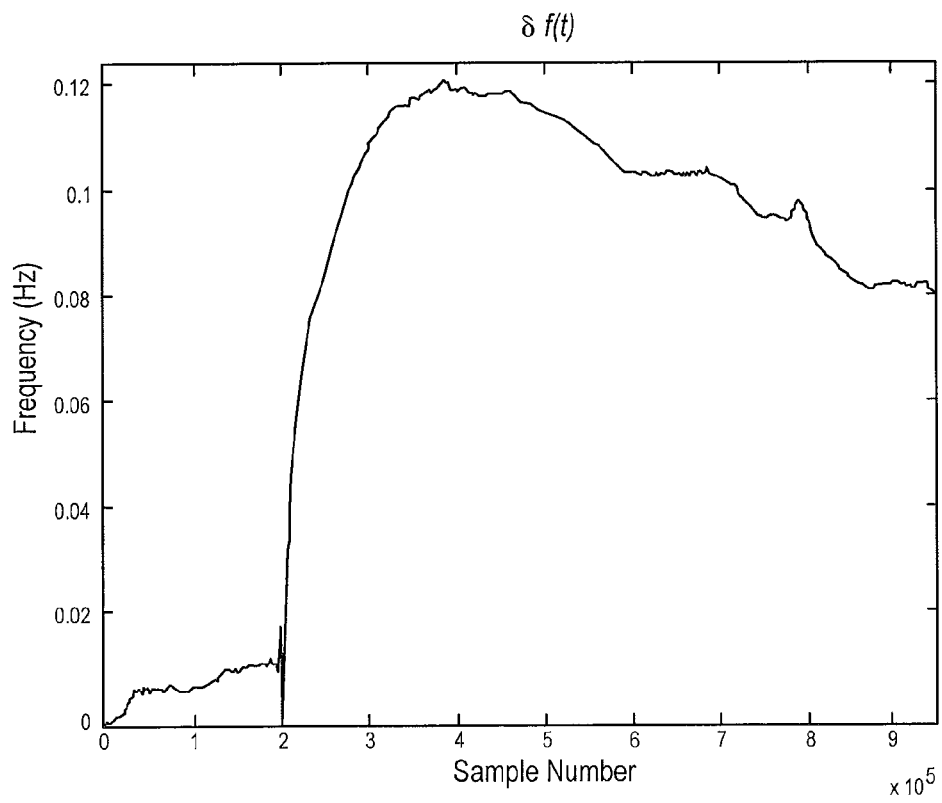
FIG. 3 is a graph of an estimated frequency deviation $\delta f(t)$ from a nominal line noise frequency $f_{LN}$, the estimated frequency deviation $\delta f(t)$ being derived from the phase deviation $\delta\phi(t)$ of FIG. 2 and including data which shows significant line noise.

FIG. 3 shows the frequency deviation δf(t) output by the first low pass filter 122 for data which shows significant line noise. The frequency deviation δf(t) of FIG. 3 may be derived from the phase deviation δφ(t) of FIG. 2 in some embodiments. During much of the sampling period shown in FIG. 3, it can be seen that the frequency deviation δf(t) is equal to about 0.1 Hz.

Figure 4:
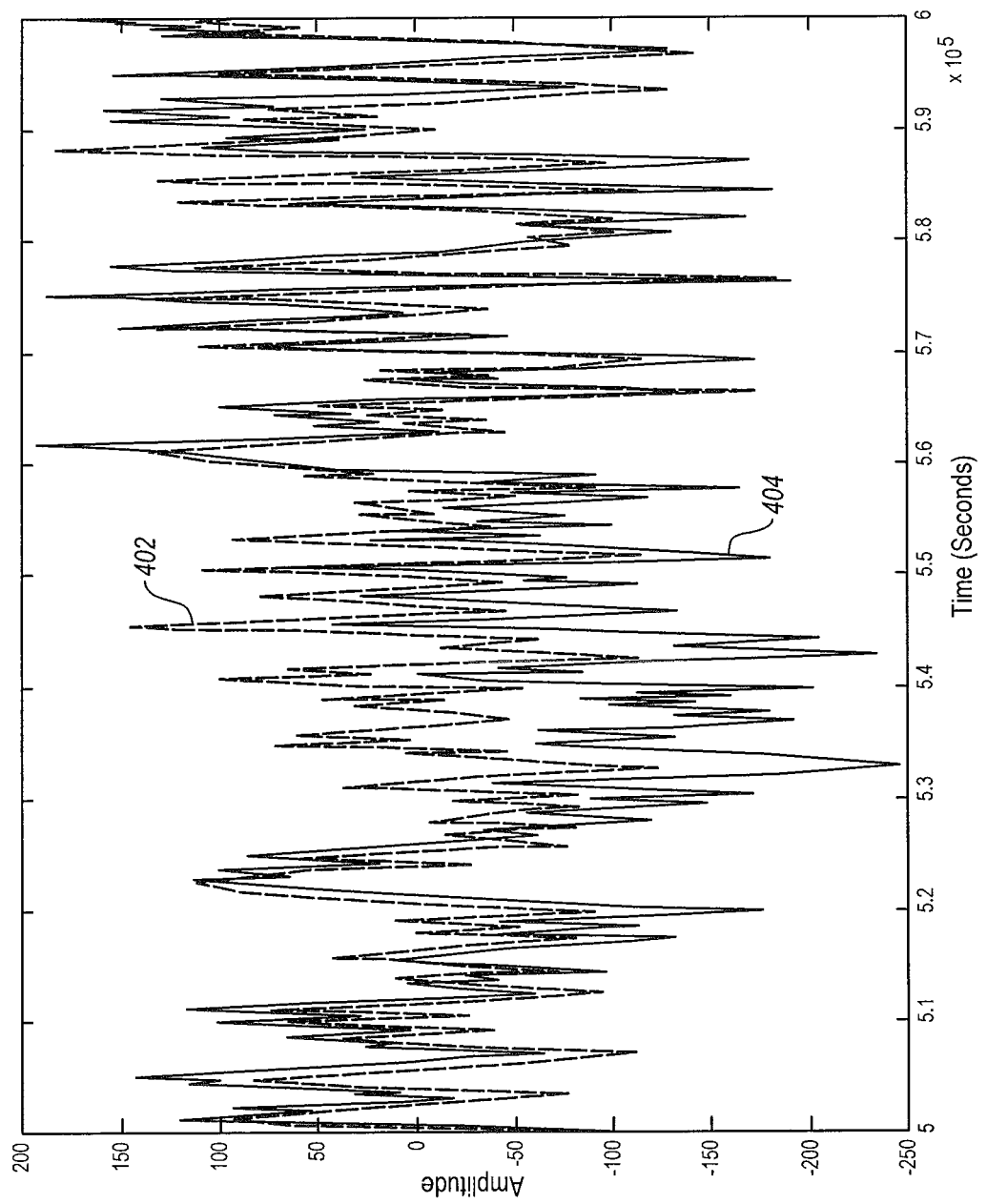
FIG. 4 is a graph of an example of a time-domain composite input signal before cancelling electrical line noise and a corresponding time-domain filtered neural signal after cancelling electrical line noise using the electrical-line-noise canceller of FIG. 1.

FIG. 4 shows a time-domain composite input signal 402 and a corresponding time-domain filtered neural signal 404 output by electrical-line-noise canceller 104 after cancelling electrical line noise in the time-domain composite input signal 402. The time-domain composite input signal 402 may correspond to the composite input signal 138 in FIG. 1 that is provided to the electrical-line-noise canceller 104 for processing. The time-domain filtered neural signal 404 may correspond to the filtered neural signal 116 in FIG. 1 output by the electrical-line-noise canceller 104.

Figure 5:
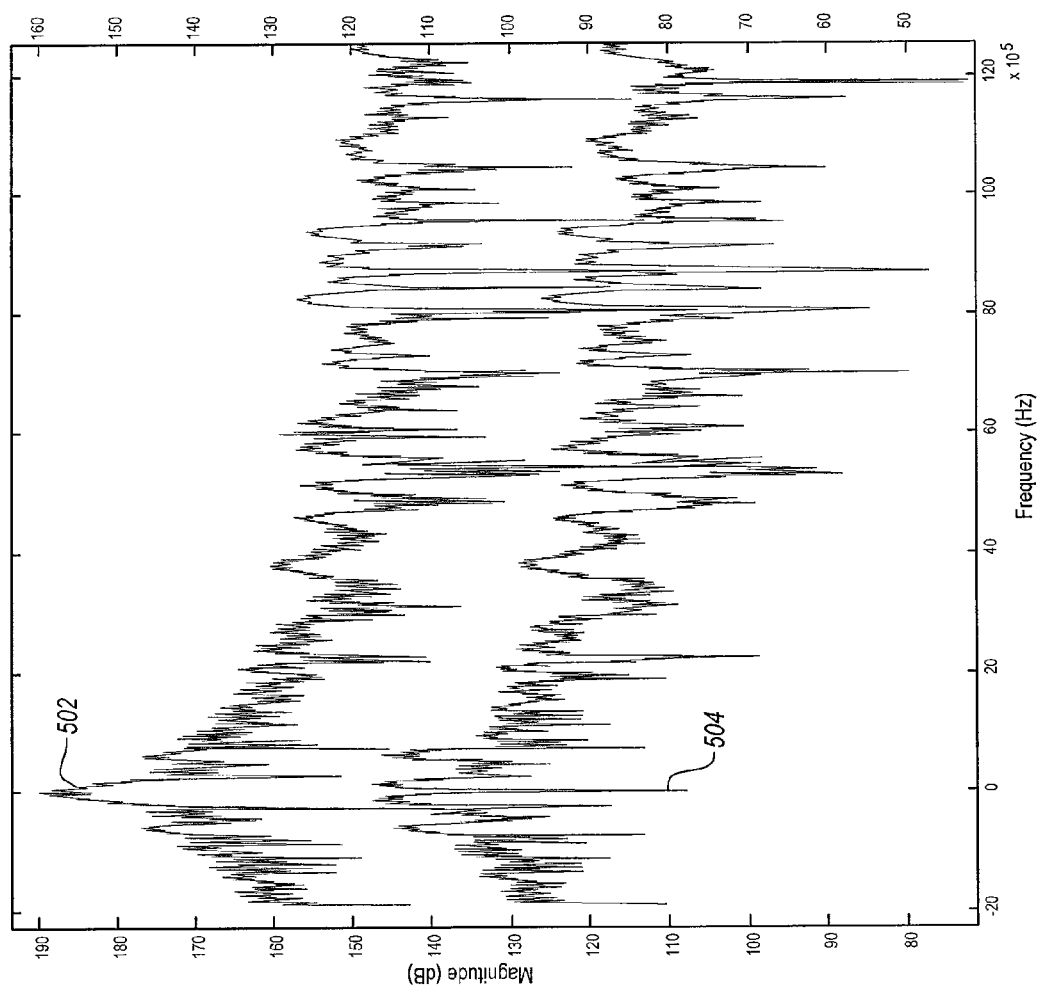
FIG. 5 is a graph of an example of a frequency-domain composite input signal before cancelling electrical line noise and a corresponding frequency-domain filtered neural signal after cancelling electrical line noise using the electrical-line-noise canceller of FIG. 1

FIG. 5 shows a frequency-domain composite input signal 502 and a corresponding frequency-domain filtered neural signal 504 output by electrical-line-noise canceller 104 after cancelling electrical line noise in the frequency-domain composite input signal 502. In the example of FIG. 5, the frequency-domain composite input signal 502 is shifted upwards relative to the frequency-domain filtered neural signal 504 by about 30 dB to clearly show each individual signal 502, 504. In FIG. 5, the right vertical axis corresponds to the frequency-domain composite input signal 502 and the left vertical axis corresponds to the frequency-domain filtered neural signal 504.

The frequency-domain composite input signal 502 may correspond to the composite input signal 138 in FIG. 1 that is provided to the electrical-line-noise canceller 104 for processing. The frequency-domain filtered neural signal 504 may correspond to the filtered neural signal 116 in FIG. 1 output by the electrical-line-noise canceller 104. In the example of FIG. 5, the frequencies of 0 Hz, 60 Hz, and 120 Hz present in the frequency-domain composite input signal 502 are substantially attenuated in the frequency-domain filtered neural signal 504 after application of the electrical-line-noise cancellation algorithm implemented by the electrical-line-noise canceller 104.

According to some embodiments, the disclosed algorithm executed by the line noise canceller 102 shown in FIG. 1 is adaptive, may be completely software-based, and can work with the current signal sampling of 30 kHz. The disclosed algorithm may further allow removal of 50 Hz and 60 Hz electrical noise even when ground loops and/or poor references are present, which is beneficial in human labs in which biological signals are being monitored. The disclosed algorithm may have a minimal effect on the frequency content of the spikes (i.e., short-burst signals from neurons are not affected). Even when the frequency of the neural signal being acquired is the same as the nominal electrical line noise, the neural signal is not removed unlike conventional notch filters. Notch filters remove real neural signals as well as electrical line noise. The disclosed algorithm only removes or substantially removes non-neural signals. One notch filter only removes fundamental frequency, while the disclosed algorithm can remove the fundamental frequency and all harmonics.

A frequency deviation of up to about 3 Hz from nominal line frequency (e.g., 60 Hz or 50 Hz) may be tolerated, and the disclosed algorithm still removes the noise, which is useful in some countries. For example, frequency deviations of up to 0.3 Hz are possible in the United States. The disclosed algorithm is responsive to phase, frequency, amplitude changes, or combinations of the foregoing. The complexity of implementation of the disclosed algorithm is minimal, using multiplication and infinite impulse response (IIR) filtering, with no need to compute sinusoids inverse. A quantized sinusoid may be used for demodulation.

II. Post-Acquisition Processing of Neural Data

Figure 6:
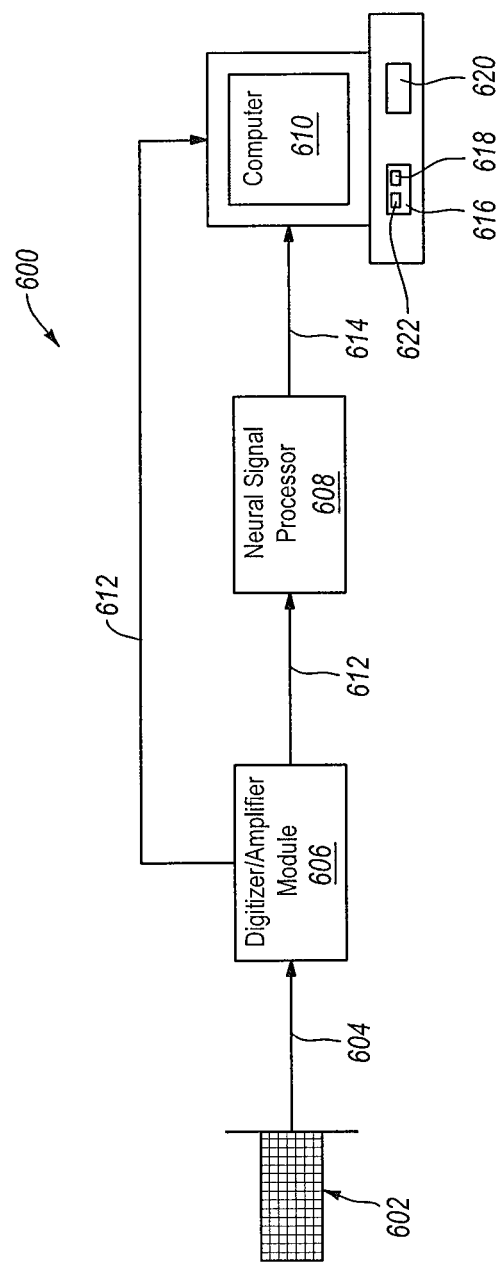
FIG. 6 is a functional block diagram of an embodiment of a neuralphysiological data acquisition system that is configured to store neural data and allow a user to process the stored neural data and view the neural data, post-acquisition, as if it is being acquired in real time.

FIG. 6 is a functional block diagram of a second embodiment of a neuralphysiological data acquisition system 600 (hereinafter "system 600"). The system 600 is configured to store neural data and allow a user to process the stored neural data and view the neural data as if it is being acquired in real time. The system 600 includes an array of microelectrodes 602 (hereinafter "array 602") configured to receive and transmit one or more analog neural signals 604. For example, the array 602 may be suitably configured to acquire analog neural signals 106 from brain tissue or peripheral nerve tissue.

The system 600 also includes a digitizer/amplifier module 606 coupled to the array 602, a neural signal processor 608 coupled to the digitizer/amplifier module 606, and a general purpose or special purpose computer 610 coupled to the digitizer/amplifier module 606 and neural signal processor 608.

The digitizer/amplifier module 606 is generally configured to amplify and digitize the analog neural signals 604 received from the array 602 to generate one or more digital neural signals 612.

The neural signal processor 608 is generally configured to perform specific types of signal processing on the neural signals 612 received from the digitizer/amplifier module 606 to generate one or more processed neural signals 614. For instance, the neural signal processor 608 may be configured to digitally filter the digital neural signals 612 based on specific filter criteria, or to detect neuron action potentials embedded in the digital neural signals 612, or to use a selected one of the microelectrodes of array 602 as a reference electrode for a selected one or more of the other microelectrodes of array 602, or to use bipolar differential reporting (i.e., taking the difference between pairs of the microelectrodes of array 602), or to filter electrical line noise as performed by the electrical-line-noise canceller 104 shown in FIG. 1, or combinations of the foregoing.

Figure 7:
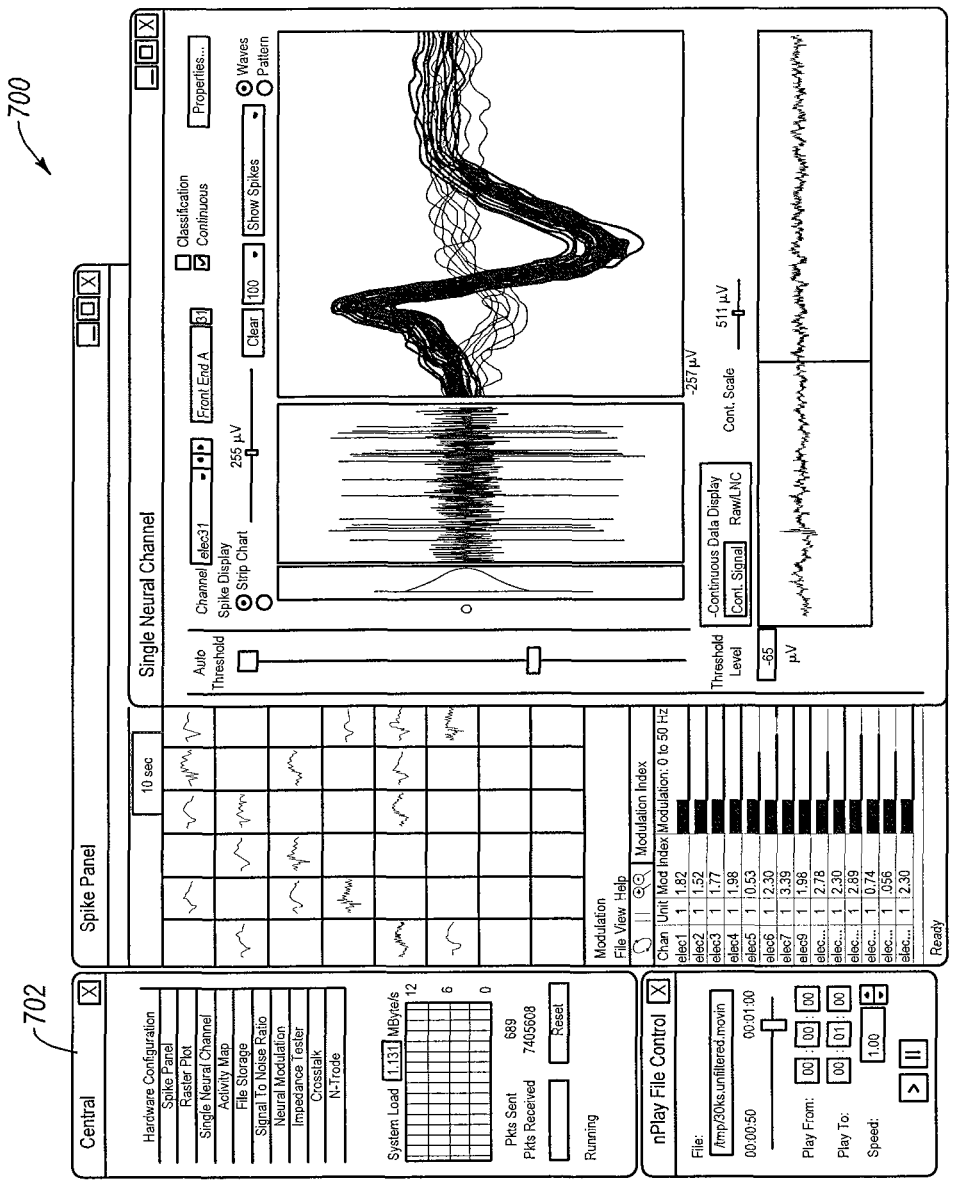
FIG. 7 is a screen shot showing an embodiment of a graphical user interface in which a number of different buttons and/or drop down menus are provided for selecting the particular technique for performing signal processing on the saved neural data.

In some embodiments, a user may select one or more of the above-described signal processing functions or other signal processing functions to be executed by the neural signal processor 608 on incoming digital neural signals 612. In this regard, FIG. 7 is a screen shot 700 of an example graphical user interface ("GUI") by which the user can configure the neural signal processor 608 to perform one of the aforementioned signal processing functions by selecting a corresponding button in, e.g., central window 702.

Returning to FIG. 6, the computer 614 is a desktop or laptop computer or other computing device suitable for performing one or more of the acts and operations described herein. For example, the computer 614 is configured in some embodiments to display the processed neural signals 614 received from the neural signal processor 608. The computer 610 is also coupled to receive unprocessed digital neural signals 612 from the digitizer/amplifier module 606 and is configured to store the digital neural signals 612 on a tangible computer-readable medium 616 as stored neural signal data 618. The computer-readable medium 616 is included in or associated with the computer 610 that additionally includes at least one processor 620. The computer-readable medium 616 may be any suitable computer-readable storage medium, such as a floppy disk, a hard disk drive, computer memory, or other suitable computer storage medium.

The computer-readable medium 616 includes a signal processing software program 622 stored thereon. The signal processing software program 622 includes computer-executable instructions that are executable by the processor 620 or other suitable computing device to perform one or more of the operations described herein. In some embodiments, the signal processing software program 622 employs the same GUI that is shown in FIG. 7, while in other embodiments the signal processing software program 622 employs any other suitable GUI. Alternately or additionally, the signal processing software program 622 is programmed in Linux or other suitable programming language.

The signal processing software program 622 stored on computer-readable medium 616 is configured to process the stored neural signal data 618 as if it is the digital neural signals 618 being received in real time and processed by the neural signal processor 608. In other words, the signal processing software program 622 emulates firmware on the neural signal processor 608 and allows the user to selectively perform one or more of the signal processing functions on the un-processed and stored neural signal data 622 that the neural signal processor 610 may perform on the digital neural signals 612.

The signal processing software program 622 in some embodiments enables a user to evaluate un-processed digital neural signals 612—e.g., in the form of stored neural signal data 618—and perform a variety of signal processing tasks on the un-processed digital neural signals 612 after experiments have been performed. For example, a user may conveniently perform any of the aforementioned signal processing functions on the stored neural signal data 618 on their laptop computer, a desktop computer, or other suitable computer, as desired. As another example, the signal processing software program 622 may be used to test a new signal processing computer program without having to run an experiment and acquire new neural data. Rather, the previously acquired digital neural signals 612 stored on computer-readable medium 616 as stored neural signal data 618 can simply be re-used.

More detail about one suitable neuralphysiological data acquisition system that may be adapted to allow un-processed digital neural signals to be transmitted to, stored in, and further processed by a computer is disclosed in the Cerebus™ Data Acquisition Users Manual, Revision 9.00, which was previously incorporated by reference.

Although the signal processing software program 622 stored on the computer-readable medium 616 is described as processing digital neural signals 612 and/or corresponding stored neural signal data 618, the disclosed embodiment may be adapted to perform any of the described signal processing tasks on analog neural signals and/or corresponding analog neural signal data. For example, the analog neural signals 604 may be amplified and stored on the computer-readable medium 616 as stored analog neural signal data (not shown in FIG. 6) and the signal processing software program 622 may process the stored analog neural signal data.

Example Methods of Operation

Figure 8:
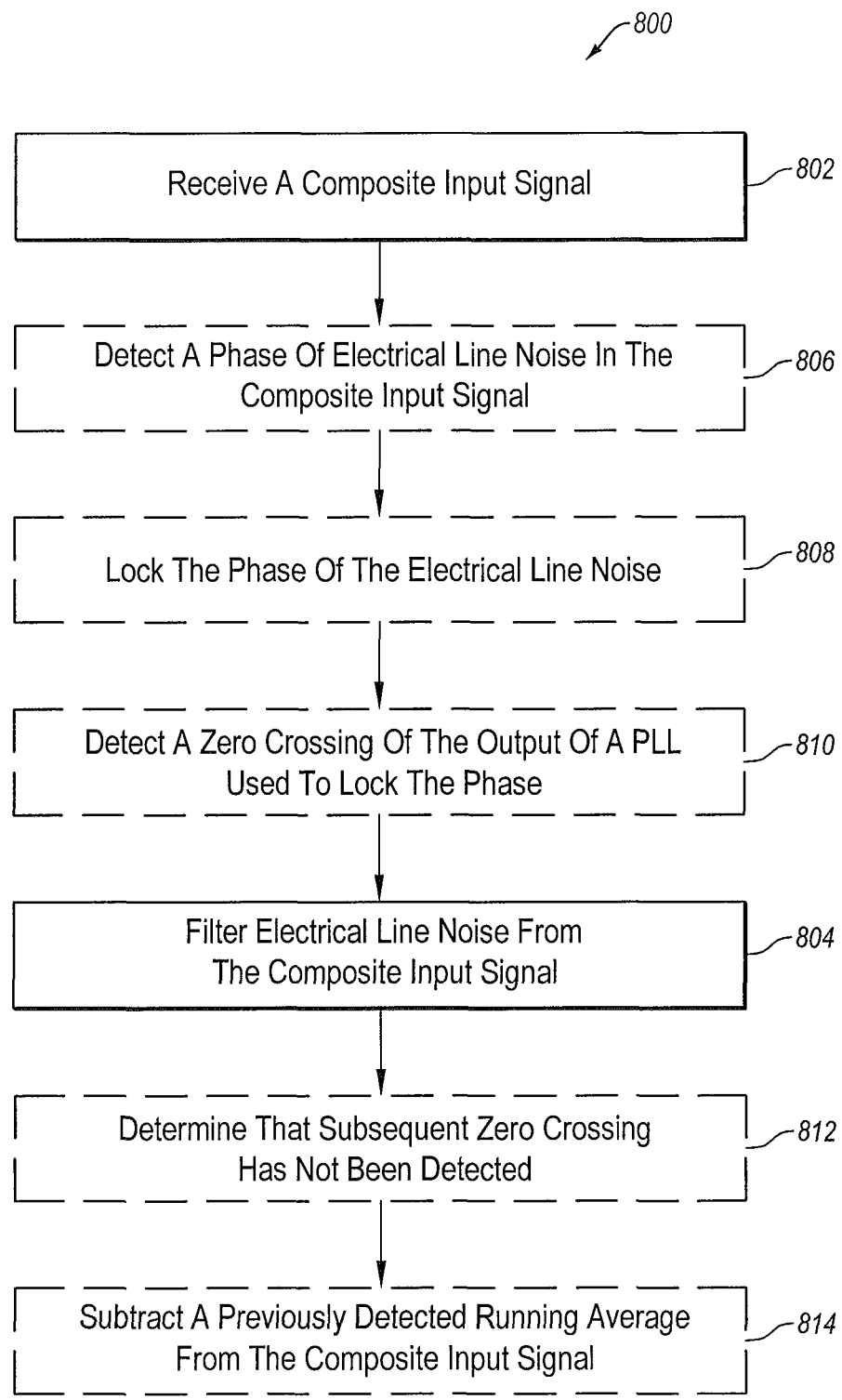
FIG. 8 shows an example flow diagram of a method of filtering electrical line noise from a composite input signal.
Figure 9:
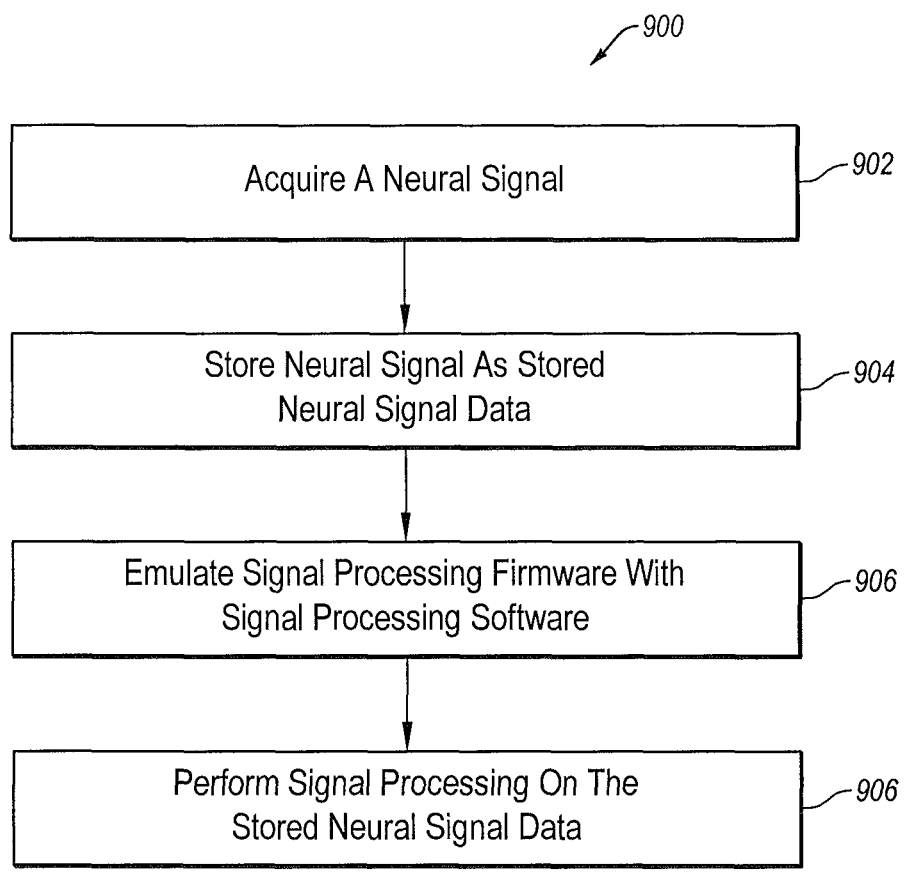
FIG. 9 shows an example flow diagram of a method of manipulating stored neural signal data.

Turning next to FIGS. 8 and 9, various example methods of operation are described according to some embodiments. One skilled in the art will appreciate that, for processes and methods disclosed herein, the acts performed in the processes and methods may be implemented in differing order than disclosed herein. Furthermore, the outlined acts and operations are only provided as examples, and some of the acts and operations may be optional, combined into fewer acts and operations, or expanded into additional acts and operations without detracting from the essence of the disclosed embodiments.

FIG. 8 is a flowchart of an example method 800 of filtering electrical line noise from a composite input signal. The method 800 of FIG. 8 is implemented in some embodiments, in whole or in part, by the neural signal processor 102 of FIG. 1, the neural signal processor 608 or computer 610 executing signal processing software program 622 of FIG. 6, or the like. More generally, the method 800 may be implemented in hardware, software, or a combination thereof.

The method 800 begins in some embodiments by receiving 802 a composite input signal from a microelectrode array of a neuralphysiological data acquisition system. For instance, act 802 may include the neural signal processor 102 receiving 802 the composite input signal 138 from array 106. In some embodiments, the composite input signal includes a neural signal, such as the digital neural signal 112, and electrical line noise, such as the electrical-line-noise waveform 140.

The method 800 additionally includes filtering 804 the electrical line noise from the composite input signal without substantially modifying the neural signal. For example, act 804 may include the adaptive filter 128 filtering 804 electrical line noise, such as electrical-line-noise waveform 140, from the composite input signal, such as composite input signal 138, to generate a filtered neural signal, such as filtered neural signal 116, using adaptive filtering as described herein. In particular, filtering 804 electrical line noise from the composite input signal includes, in some embodiments, the adaptive filer 128 running an average over the composite input signal 138 for one cycle beginning at a detected zero crossing and removing the running average from the composite input signal 138 for the cycle.

Although not required, in some embodiments, the method 800 of FIG. 8 further includes one or more of acts 806, 808, 810, 812 and 814. For instance, at act 806, a phase of the electrical line noise in the composite input signal is detected. Act 806 may include the phase detector 118 detecting the phase of the electrical-line-noise waveform 140 in the composite input signal 138, for example.

At act 808, the phase of the electrical line noise in the composite input signal is locked. Act 808 may include the PLL 124 locking to the phase of the electrical-line-noise waveform in the composite input signal 138 and outputting phase deviation δϕ(t), for instance.

At act 810, a zero crossing of the output of the PLL 124 is detected. Act 810 may include the zero-crossing detector 126 determining that the output, e.g., phase deviation δϕ(t), is below a predetermined threshold, such as $2\pi^*f_{LN}/f_s$, and that a predetermined minimum number of samples of the output of the PLL 124 have been taken since a previously detected zero crossing.

The zero crossing detected at act 801 may be referred to as an initial detected zero crossing. At act 812, it is determined that an expected subsequent zero crossing has not been detected. Act 812 may include the zero-crossing detector 126 determining that the output of PLL 124 has not been detected below the predetermined threshold within a predetermined maximum number of samples since the initial detected zero crossing.

At act 814, and in response to determining 812 that the expected subsequent zero crossing has not been detected, a previously calculated running average is subtracted from the composite input signal until another zero crossing is detected. Act 814 is performed in some embodiments by adaptive filter 128.

Turning next to FIG. 9, a flowchart is disclosed of an example method 900 of manipulating stored neural signal data. The method 900 of FIG. 9 is implemented in some embodiments, in whole or in part, by the computer 610 executing signal processing software program 622 of FIG. 6, or the like. More generally, the method 900 may be implemented in hardware, software, or a combination thereof.

The method 900 begins in some embodiments by acquiring 902 a neural signal from a neuralphysiological data acquisition system. For example, act 902 includes, in some embodiments, the computer 610 of FIG. 6 receiving one or more digital neural signals 612 from the digitizer/amplifier module 606. In other embodiments, the neural signal acquired by the computer 610 is an analog neural signal.

At 904, the neural signal is stored on a computer-readable medium as stored neural signal data. Act 904 may include the computer 610 storing neural signal data 618 representative of digital neural signals 612 on the computer-readable medium 616.

At 906, signal processing firmware of the neuralphysiological data acquisition system is emulated with signal processing software executed by a computing device. Act 906 may include the computer 610 executing signal processing software program 622 to emulate neural signal processor 608.

At 908, signal processing is performed on the stored neural signal data using the signal processing software. The act 908 of performing signal processing on the stored neural signal data may include one or more of: filtering the neural signal represented by the stored neural signal data based on specific filter criteria, detecting neuron action potentials embedded in the neural signal; using a particular microelectrode in an array of microelectrodes of the neuralphysiological data acquisition system as a reference electrode, performing bipolar differential reporting, or filtering electrical line noise from the neural signal.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The embodiments described herein may include the use of a special purpose or general-purpose computer including various computer hardware or software modules, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, examples of tangible computer-readable media include RAM, ROM, EEPROM, CD-ROM or other optical disk storage, magnetic disk storage or other magnetic storage devices, or any other medium which can be used to carry or store desired software programs in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "program" can refer to software objects or routines that execute on the computing system. The different programs described herein may be implemented as objects or processes that execute on a computing system (e.g., as separate threads). While some embodiments described herein can be implemented in software, implementations in hardware or a combination of software and hardware are also possible and contemplated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A neuralphysiological data acquisition system comprising:
an electrode array configured to receive and transmit analog neural signals;
a digitizer/amplifier module coupled to the electrode array and configured to amplify and convert the analog neural signals to digital neural signals; and
a neural signal processor comprising an electrical-line-noise canceller coupled to the digitizer/amplifier module and configured to receive a composite input signal comprising the digital neural signals and electrical line noise, wherein the electrical-line-noise canceller is further configured to selectively filter the electrical line noise from the composite input signal and output filtered neural signals, wherein the electrical-line-noise canceller includes:
  a phase detector configured to receive and detect a phase of the composite input signal, the phase detector including:
    a sinusoid generator configured to generate a sinusoid for multiplication by the composite input signal to generate a demodulated noise signal
    a low pass filter configured to receive the demodulated noise signal;
    a proportional-integral-derivative controller coupled to the low pass filter; and
    a phase interpolator coupled to the proportional-integral-derivative controller;
  a phase lock loop coupled to the phase detector and configured to lock to the phase of the electrical line noise;
  a zero-crossing detector coupled to the phase lock loop and configured to detect zero crossings of an output of the phase lock loop; and
  an adaptive filter coupled to the zero-crossing detector and configured to remove the electrical line noise from the composite input signal and output the filtered neural signals that are substantially similar to the digital neural signals; and wherein:
  the composite input signal is modeled as:

$x(t)=N(t)+A(t)\sin(2\pi(f_{LN}+\delta f(t))t+\delta\phi(t))$, where $N(t)$ is the input neural signal, $A(t)$ is an amplitude signal of the electrical line noise, t is a variable representing time, $f_{LN}$ is nominal line noise frequency of the electrical line noise, $\delta f(t)$ is frequency deviation of the electrical line noise from nominal frequency $f_{LN}$, and $\delta\phi(t)$ is phase deviation of the electrical line noise;

the sinusoid is modeled as:

$y(t)=\cos(\phi(t)-\pi/2)$, where $\phi(t)$ is estimated phase of the electrical line noise; and
  $\phi(t)$ is modeled as:

$\phi(t)=2\pi f_{LN}*t+\Delta\phi(t)$, where $\Delta\phi(t)$ is estimated phase difference $\Delta\phi_e(t)$ output by the proportional-integral-derivative controller once every D samples, or interpolated phase difference $\Delta\phi_i(t)$ output by the phase interpolator for every sample in between the D-sampled estimated phase difference $\Delta\phi_e(t)$, or phase deviation $\delta\phi(t)$ output by the phase lock loop; and the low pass filter is configured to output an error signal that is valid once every D samples and that is modeled as:

$\text{error}(t)=B(t)\sin(\Delta\phi_e(t))$, where $B(t)$ is an approximation of $A(t)$;
  the proportional-integral-derivative controller is configured to output estimated phase difference $\Delta\phi_e(t)$ once every D samples that is also output by the phase interpolator once every D samples to the phase lock loop, where estimated phase difference $\Delta\phi_e(t)$ is modeled as:

$\Delta\phi_e(t)=K_p*\text{error}(t=n*D)+K_i*(\Delta\phi_e(t=n*D-D)+\text{error}(t=n*D)*1/f_s)+K_d*(\text{error}(t=n*D)-\text{error}(t=n*D-D))$, where $K_p$, $K_i$, and $K_d$ are, respectively, a proportional weighting factor, an integral weighting factor, and a derivative weighting factor of the proportional-integral-derivative controller, n is 0, 1, 2, 3, ..., error(t=n*D) represents the output of the low pass filter at a particular valid time sample t=n*D, $\Delta\phi_e(t=n*D-D)$ represents estimated phase difference $\Delta\phi_e(t)$ at an immediately preceding valid time sample t=n*D-D, $f_s$ is a sampling frequency of the phase detector, and error(t=n*D-D) represents the output of the low pass filter at the immediately preceding valid time sample t=n*D-D.

2. The neuralphysiological data acquisition system of claim 1, wherein the electrical-line-noise canceller further comprises:
  a differentiator coupled to an output of the phase lock loop; and
  a low pass filter coupled between an output of the differentiator and an input of the phase interpolator.

3. The neuralphysiological data acquisition system of claim 1, wherein the neural signal processor is configured to perform a plurality of signal processing functions.

4. The neuralphysiological data acquisition system of claim 3, wherein the signal processing function comprises at least one of:
  digital filtering of the digital neural signals based on specific filter criteria;
  detection of neuron action potentials embedded in the digital neural signals;
  use of a particular electrode of the electrode array as a reference electrode; or
  use of bipolar differential reporting.

5. The neuralphysiological data acquisition system of claim 1, further comprising a computer coupled to an output of the electrical-line-noise canceller and configured to receive and display the filtered neural signals.

6. The neuralphysiological data acquisition system of claim 5, wherein the computer is coupled to an output of the digitizer/amplifier module and is further configured to receive and store the digital neural signals on a non-transitory computer-readable medium as stored neural signal data.

7. The neuralphysiological data acquisition system of claim 6, wherein the non-transitory computer-readable medium includes stored thereon computer-executable instructions that are executable by the computer to emulate the neural signal processor by performing a signal processing function on the stored neural signal data that is the same as a signal processing function performed by the neural signal processor on the digital neural signals.

8. The neuralphysiological data acquisition system of claim 1, wherein:
  the phase interpolator is configured to output interpolated phase difference $\Delta\phi_i(t)$ for every sample in between the D-sampled estimated phase difference $\Delta\phi_e(t)$, where interpolated phase difference $\Delta\phi_i(t)$ is modeled as:

$\Delta\phi_i(t)=\Delta\phi_e(t=n*D)+2\pi*(f_{LN}+\delta f(t))*(n*D-D)$, the phase lock loop is configured to receive estimated phase difference $\Delta\phi_e(t)$ once every D samples from the phase interpolator and to receive interpolated phase difference $\Delta\phi_i(t)$ for every sample in between the D-sampled estimated phase difference $\Delta\phi_e(t)$, and the phase lock loop is further configured to output phase deviation $\delta\phi(t)$ to the sinusoid generator, a zero-crossing detector, and a differentiator included in the electrical-line-noise canceller; and the differentiator is configured to differentiate consecutive samples of the phase deviation $\delta\phi(t)$ to calculate frequency deviation $\delta f(t)$ which is filtered to remove noise from the calculated frequency deviation $\delta f(t)$, wherein the filtered frequency deviation $\delta f(t)$ is fed back into the phase interpolator to calculate the interpolated phase difference $\Delta\phi_i(t)$ for every sample in between the D-sampled estimated phase difference $\Delta\phi_e(t)$.

* * * * *